US009603886B1

(12) United States Patent
Laning

(10) Patent No.: US 9,603,886 B1
(45) Date of Patent: Mar. 28, 2017

(54) METHOD FOR TREATING A HANGOVER

(71) Applicant: George Jordan Laning, Palo Alto, CA (US)

(72) Inventor: George Jordan Laning, Palo Alto, CA (US)

( * ) Notice: Subject to any disclaimer, the term of this patent is extended or adjusted under 35 U.S.C. 154(b) by 0 days.

(21) Appl. No.: 14/283,594

(22) Filed: May 21, 2014

Related U.S. Application Data

(63) Continuation of application No. 13/310,684, filed on Dec. 2, 2011, now abandoned.

(60) Provisional application No. 61/458,972, filed on Dec. 3, 2010.

(51) Int. Cl.
*A61K 36/48* (2006.01)
*A61K 36/8962* (2006.01)
*A61K 36/42* (2006.01)
*A61K 36/28* (2006.01)

(52) U.S. Cl.
CPC .......... *A61K 36/8962* (2013.01); *A61K 36/28* (2013.01); *A61K 36/42* (2013.01)

(58) Field of Classification Search
CPC ................................ A23F 3/00; A61K 36/738
USPC .... 426/2, 615, 648, 518, 519, 521; 424/757, 424/602
See application file for complete search history.

(56) References Cited

U.S. PATENT DOCUMENTS

| | | | | |
|---|---|---|---|---|
| 4,006,219 A | * | 2/1977 | Upham et al. | 424/94.1 |
| 4,165,376 A | * | 8/1979 | Rosenberg | 514/325 |
| 4,594,249 A | * | 6/1986 | Procter et al. | 424/125 |
| 8,507,015 B2 | * | 8/2013 | Thorsby et al. | 424/729 |
| 2006/0045929 A1 | * | 3/2006 | Lee | 424/757 |
| 2006/0112584 A1 | * | 6/2006 | Jones | 34/60 |
| 2006/0222682 A1 | * | 10/2006 | Andrews | A61K 36/185 424/439 |
| 2008/0299284 A1 | * | 12/2008 | Jang | 426/597 |
| 2010/0183736 A1 | * | 7/2010 | Hays | A61K 36/9068 424/602 |
| 2011/0052735 A1 | * | 3/2011 | Zur Wiesche et al. | 424/732 |

OTHER PUBLICATIONS

Xu et al., "Natural Medicines for Alcoholism treatment: A Review", Drug and Alcohol Review (Nov. 2005), 24, 525-536.*
Filiponne, "Cure-Bananas," About.com Guide, Jan. 1, 2005, p. 1, http://homecooking.about.com/b/2005/01/hangover-cure-bananas.htm.
Buddy T, "The Cures and Remediess for Hangovers," About.com Guide, pp. 1 and 2, Nov. 25, 2010, http://alcoholism.about.com/od/hangovers/a/cures/htm.
Krishan, Shubhra, "16 Superb Health Benefits of Cucumber," Care 2 Healthy Living, Jun. 13, 2013 pp. 1-8, www.care2.com/greenliving/16-superb-health-benefits-of-cucumber.html.
"Cirrhosis," MedlinePlus, Dec. 23, 2010, www.nlm.nih.govmedlineplus/cirrhosis.html.
"Folate Deficiency Anemia," New York Presbyterian Hospital, Nov. 30, 2008, nyp.org/health/blood-folate.html.
Reviewed by Kimball Johnson, MD., "What is Gastritis?" WebMD, Jul. 7, 2012, pp. 1-2, WebMD, LLC.
Raisbeck, Aurora, "Health Benefits of Onions," Foods-Healing-Power.com, pp. 1-12, www.foods-healing-power.com/health-benefits-of-onions.html.
"Cucumber, with Peel, Raw," SELF Nutrition Data, pp. 1-4, nutritiondata.self.com/facts/vegetables-and-vegetable-products/2439/2.
"Lettuce, Cos or Romaine, Raw," SELF Nutrition Data, pp. 1-4, nutritiondata.self.com/facts/vegetables-and-vegetable-products/2475/2.
"Turnip Greens, Cooked, Boiled, Drained, without Salt," SELF Nutrition Data, pp. 1-4, nutritiondata.self.com/facts/vegetables-and-vegetable-products/2704/2.
"Which foods are acidic?" Columbia Health, Sep. 12, 2003, pp. 1-3, goaskalice.columbia.edu/which-foods-are-acidic.
Du Toit, Alexandra, "10 Health Benefits of Cucumbers," Natural News, Aug. 11, 2012, pp. 1-9, www.naturalnews.com/036769_cucumbers_health_benefits_rehydration.html#.
George Washington University, Health Promotion and Prevention Services,Colonial Health Center, "Alcohol Absorption," http://prevention.gwu.edu/alcohol-absorption.
Loyola Marymount University, "Blood Alcohol Content," http://academics.lmu.edu/headsup/forstudents/bloodalcoholcontent/.
Barbara Bates, FitDay, "Alkaline vs. Acidic Foods: What This Means to You," http://www.fitday.com/fitness-articles/fitness/alkaline-vs-acidic-foods---what-this-means-to-you.html#6.
"A list of Acid / Alkaline Forming Foods," http://www.rense.com/1.mpicons/acidalka.htm.
Altered States, "Monitoring your Body's PH levels," http://altered-states.net/barry/update178/.
Jerry R. Balentine, Do, Facep, "Alcohol Intoxication Causes," http://www.emedicinehealth.com/alcohol_intoxication/page3_em.htm.
Virtual Medical Center, "Alcohol Hangovers," Jan. 21, 2011 (Modified: Sep. 29, 2015), http://www.myvmc.com/lifestyles/alcohol-hangovers/.
SELF Nutrition Data, http://nutritiondata.self.com/facts/vegetables-and-vegetable-products/2475/2.

* cited by examiner

*Primary Examiner* — Nina Bhat

(57) ABSTRACT

A juice drink for hangover treatment containing juiced ingredients of red onion, cucumber, and a leafy green vegetable, such as romaine lettuce to treat a hangover after consumption of alcohol.

18 Claims, 8 Drawing Sheets

| Name | Age | Sex | Average Drinks Consumed in a night | Severity of Hangover* | Results After 5 Minutes | Results After 1 Hour | Results After 2 Hours | Results After 4 Hours |
|---|---|---|---|---|---|---|---|---|
| Jason | 29 | M | 6 | 6 | Improved | No hangover | No hangover | No hangover |
| Stephanie | 24 | F | 10 | 6 | Improved | Improved | Same | No hangover |
| Grady | 25 | M | 16 | 8 | Improved | Improved | Improved | No hangover |
| Derek | 30 | M | 10+ | 4 | Improved | Improved | Improved | No hangover |
| Anna | 30 | F | 6 | 6 | Improved | Same | Improved | No hangover |
| Christine | 29 | F | 5 | 4 | Same | Improved | Improved | No hangover |
| Nate | 28 | M | 8 | 5 | Same | Same | Improved | No hangover |
| Jeffrey | 37 | M | 4-8 | 5 | Same | Same | Improved | No hangover |
| Roxanne | 29 | F | 8 | 6 | Same | Improved | Improved | Improved, No hangover after 6 hours |
| Amanda | 33 | F | 10 | 10 | Same | Improved | Improved | Improved to a Severity of 3 |

*Severity of hangover is rated on a scale of 1 to 10, with 1 being least hung-over and 10 being most hung-over

US 9,603,886 B1

METHOD FOR TREATING A HANGOVER

CROSS-REFERENCE TO RELATED APPLICATIONS

This application is a continuation-in-part application of U.S. patent application Ser. No. 13/310,684, filed Dec. 2, 2011, now abandoned, which claims the benefit of Provisional Application No. 61/458,972, filed Dec. 3, 2010, which applications are incorporated here in their entirety by this reference.

STATEMENT REGARDING FEDERALLY SPONSORED RESEARCH OR DEVELOPMENT

No federally sponsored research or development.

THE NAMES OF THE PARTIES TO A JOINT RESEARCH AGREEMENT

No parties to a joint research agreement.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

No prior disclosures by the inventor or a joint inventor

BACKGROUND OF THE INVENTION

Hangover is the generic term for the ailments associated with alcohol related sickness. These ailments include weak stomach, vomiting, upset stomach, acidic stomach, nausea, dehydration, elevated body temperature, rapid heart rate, heart palpitations, difficulty concentrating, bloodshot eyes, trouble sleeping, depression, anxiety, irritability, sensitivity to light and noise, blurred vision, dizziness, cold sweats, muscular weakness, fatigue, muscle aches, general pain, labored breathing, erratic motor functions, headache, and inability to digest water into the hydration process. In the past hangovers were treated by using pain medicines, but these medicines caused stomach bleeding and only helped to reduce headaches.

Thereafter, several types of hangover remedies have been produced coming in many different forms. These remedies come in pill form, as an effervescent drink additive, and as a health tea. All of these attempts to remedy a hangover contain various vitamins, minerals, and chemicals to combat the symptoms. These methods give inconsistent results due to the unregulated intake of these vitamins, minerals, and chemicals by the human body. Excess amounts of certain vitamins, minerals, and chemicals also bring about unwanted side effects and imbalances in the body's chemistry.

The method for producing known products can also be long and time consuming, making them difficult to streamline for production and costly. The method taught in U.S. Patent Publication No. 2008/0299284 (hereinafter Jang's health tea) involves slicing vegetables and drying them in the sun. This manual operation takes days to complete. This process of production is also heavily impacted by weather and season. The time wasted is costly for the producer who must consider labor, overhead, and production capacity into their business plan.

Some pills, drink additives, and health teas are a combination of many multiple elements which makes them more costly and difficult to produce. Jang's health tea does not contain all the necessary ingredients to completely remedy a hangover. Instead, Jang's health tea uses a list of 14 different elements in combination to create the product. A reduction in unnecessary elements is a reduction in costs to labor, materials, and manufacturing overhead. Useless elements are wasteful and do not add benefits to the product.

A lack of vitamins and minerals can also be a problem associated with these approaches. Jang's health tea contains minute quantities of vitamins and minerals and is focused more on the soothing aspects of hot water which lacks effectiveness in remedying a hangover. The health tea comforts the hung-over individual without effectively treating the symptoms to eradicate them. It is well known that 4, 8, 12, or 16 ounces of liquid tea prepared from tea bags contain a small amount of nutrients as compared to 4, 8, 12, or 16 ounces of a juice from fruits or vegetables, respectively.

Serious side-effects can also be a problem associated with these approaches. Jang's health tea contains ginkgo leaves which when consumed in excess can be toxic as described in the detailed description section of Jang's invention. Jang's health tea contains *Ganoderma lucidum* which when consumed in excess can cause adverse effects as explained in the detailed description section of Jang's invention. Jang's health tea contains roots of sprout beans and *Hedysarum* which can both, when consumed in excess, adversely affect the body of a person who has weak kidney function as described in the detailed description section of Jang's invention. Weak kidney function is common in alcoholic drinkers and can lead to wide spread adverse effects among users of the health tea. Jang's health tea contains *Maximowiczia typica* which when consumed in excess can cause excessive sweating and adverse effects as described in the detailed description section of Jang's invention. The side-effects of some hangover treatments can be dangerous and counterproductive for users, especially when those users are already feeling the adverse effects of an alcoholic hangover.

Seasonality can also be a problem associated with these approaches. Some fruits and vegetables used in hangover treatments are seasonal and are in short supply during the off season months of the year. This makes it difficult and expensive to meet the needs of demand year round. For example, Jang's health tea has a component of persimmons which is seasonal. Persimmons are in season from approximately October to February every year in the United States. The rest of the year persimmons are in short supply. This effectively reduces the production of Jang's health tea during the time period between March and September. Alcohol consumption is year round and the seasonality of some hangover treatments can lead to shortages of those treatments. Shortages of some hangover treatments can cause problems for drinkers that rely on those hangover treatments for their hangover needs.

The Applicant's hangover treatment is a successful implementation of an ancient idea where others have failed and also a solution to a long-felt, long-existing, and unsolved need since alcohol was invented. It has been perceived to be insolvable. Hangovers are a worldwide pandemic affecting all humans that consume enough alcohol to induce a hangover. It is a problem for modern society that has not been given a solution until the creation of the Applicant's invention.

Humans have tried for a long time to come up with a remedy for hangover symptoms, but none have been successful in properly treating an individual once hangover symptoms are present. All other hangover remedies have only been useful for soothing or masking a hangover but none have been able to eliminate hangover symptoms within a span of 4 hours. For example, Jang's health tea has 14 components and is only used to reduce intoxication of individuals before and during drinking liquor. Jang's health tea is used to reduce the effects of alcohol at the time of consumption of alcohol and prevent alcohol intoxication by consumption of the health tea before drinking the alcohol. Jang's health tea is not meant for the purpose of hangover treatment once hangover symptoms become present, normally occurring the following day after drinking alcohol.

BRIEF SUMMARY OF THE INVENTION

Applicant's invention contains three components and may be used to eliminate hangover symptoms of individuals the day after drinking when the hangover symptoms have taken effect. Applicant's invention of a combination of red onion juice, cucumber juice, and a leafy green vegetable juice may be able to alleviate the symptoms of hangover. Applicant is the first to successfully invent a workable remedy for the hangover that eliminates symptoms and restores the individual to normal health. The components of the applicant's invention create a novel synergistic effect because the combination creates a greater effect than the sum of the effects of the components separately.

Since a hangover normally occurs the day after an individual has been drinking alcohol and the symptoms present themselves once that individual is no longer intoxicated, Applicant's invention is useful because it treats an individual who is suffering from already-present hangover symptoms. Applicant's invention is meant to help individuals who are no longer intoxicated, but are still feeling the effects of a hangover. In accordance with one embodiment, a hangover treatment comprises cucumber juice, red onion juice, and romaine lettuce juice served fresh for consumption or processed for storage.

Accordingly several advantages of one or more aspects are as follows: to treat more ailments of a hangover; to allow the body to process a safe and naturally regulated amount of vitamins, minerals, and chemicals through natural juice consumption; and to provide sufficient vitamins, minerals, and chemicals to effectively treat hangover symptoms. Also, applicant's invention provides a hangover remedy that is: produced quickly, mass-manufactured with relative ease, produced with less time and effort, produced without reliance on weather, consumable immediately at the moment of need without preparation, producible year round with readily available components that are not limited by a seasonal availability, and made from natural ingredients that are safe for consumption. Other advantages of one or more aspects will be apparent from a consideration of the drawings and ensuing description.

BRIEF DESCRIPTION OF THE DRAWINGS

FIG. 8 shows an example of a study of the effectiveness of the composition and method of the Hangover Treatment.

DETAILED DESCRIPTION OF THE INVENTION

The detailed description set forth below in connection with the appended drawings is intended as a description of presently-preferred embodiments of the invention and is not intended to represent the only forms in which the present invention may be constructed and/or utilized. The description sets forth the functions and the sequence of steps for constructing and operating the invention in connection with the illustrated embodiments. However, it is to be understood that the same or equivalent functions and sequences may be accomplished by different embodiments that are also intended to be encompassed within the spirit and scope of the invention.

Figure 1:
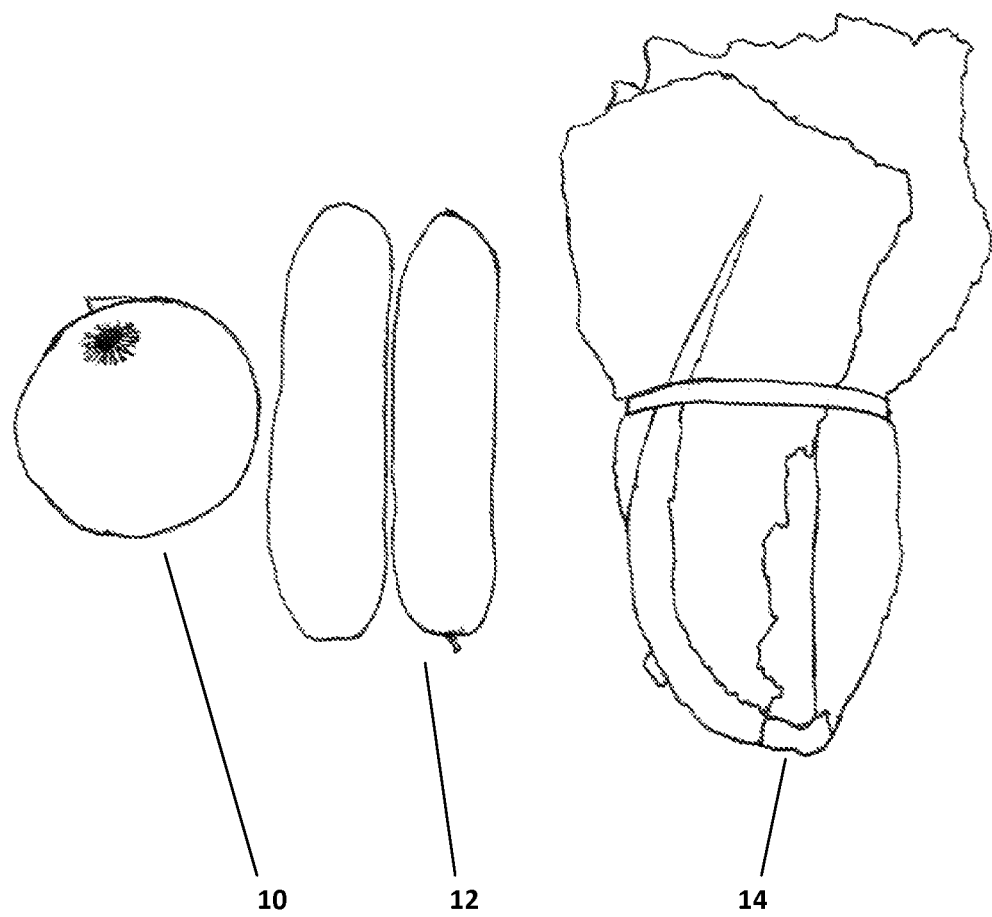
FIG. 1 shows raw elements for one embodiment of the Hangover Treatment.

The components of the applicant's invention produce a new and unexpected result because when combined, they do more than their usual function individually. Red onion alone does not alleviate the symptoms of a hangover; cucumber alone does not alleviate the symptoms of a hangover; and romaine lettuce, butterhead lettuce, oakleaf lettuce, turnip greens, or spinach alone do not alleviate the symptoms of a hangover. However, the combination of red onion juice, cucumber juice, and a leafy green vegetable is able to alleviate the symptoms of hangover. The physical features of the applicant's invention are novel and different from the above references because the applicant's invention is composed of a juice taken directly from the vegetables and contains only 3 ingredients. The hangover treatment comprises of a red onion 10, a cucumber 12, and a leafy green vegetable. Preferably, the leafy green vegetable is romaine lettuce 14. FIG. 1 shows raw elements for one embodiment of the hangover treatment. To create other embodiments of the hangover treatment, romaine lettuce 14 as shown in FIG. 1 can be substituted for one or more leafy green vegetables including butterhead lettuce 15, oakleaf lettuce 16, turnip greens 17, or spinach 18. Flavorings for new embodiments such as pineapple juice, agave syrup, and sweeteners may be added to an embodiment and may change with market preferences and after ongoing market research.

The amount of the red onion 10, cucumber 12, and leafy green vegetable that is required to be consumed, however, is too much for most individuals to eat raw because of its flavor and harsh nature. An individual will likely have to eat approximately 1.5 to approximately 4 ounces of red onions (chopped and with the roots removed), approximately 4 to approximately 11 ounces of cucumbers (peeled and sliced), and approximately 4 to approximately 9 ounces of leafy green vegetables (washed and shredded into edible sized pieces) to consume the effective amount for treating a hangover. Thus it is very likely that if an individual were to try to eat the effective amount of red onion, the individual would probably not be able to and would likely throw up. The other ingredients in their raw form that must be consumed to treat the hangover are also difficult for a hung-over individual to consume because of the nature of their illness which makes consumption of solid foods difficult. A hungover individual would have difficulty eating the ingredients in their raw form since they would probably be too sick to ingest the composition.

The amount of the hangover treatment necessary to treat hangover symptoms is at least 2 to 4 ounces of juice. More juice is necessary for hangovers of greater intensities and more doses may be required for lingering hangovers. The average effective hangover treatment is between 5 and 20 ounces. Preferably, users are likely to drink 5 to 15 ounces or more preferably 8 to 12 ounces.

Red onion juice is present in an amount ranging from approximately 5 percent to approximately 30 percent of the total weight of the juice. Preferably, the red onion juice is present at approximately 10 percent to approximately 25 percent. Most preferably, the red onion juice is present at approximately 15 percent of the total weight of the juice. If the total weight of the juice contains less than 5 percent red onion juice the drink will not be effective because the drink will not cleanse the body. If the total weight of the juice contains more than 30 percent red onion juice the flavor will be too harsh, the drink will be very difficult to consume, and the drink may induce vomiting.

Cucumber juice is present in an amount ranging from approximately 15 percent to approximately 80 percent of the total weight of the juice. Preferably, the cucumber juice is present at approximately 30 percent to approximately 70 percent. Most preferably, the cucumber juice is present at approximately 52.5 percent of the total weight of the juice. If the total weight of the juice is less than 15 percent cucumber juice, the drink will not be effective because the acid in your stomach will not be neutralized or subside. If the total weight of the juice is more than 80 percent cucumber juice the drink will contain either too little leafy green vegetable juice or too little red onion juice to be effective.

Leafy green vegetable juice is present in an amount ranging from approximately 15 percent to approximately 80 percent of the total weight of the juice. Preferably, the leafy green vegetable juice is present at approximately 20 percent to approximately 60 percent. Most preferably, the leafy green vegetable juice is present at approximately 32.5 percent of the total weight of the juice. If the total weight of the juice is less than 15 percent leafy green vegetable juice, the drink will not be effective because the juice will lack vitamins and nutrients. If the total weight of the juice is more than 80 percent leafy green vegetable juice, the drink will contain either too little red onion juice or too little cucumber juice to be effective.

By way of example only, these amounts, when including a flavoring such as pineapple juice, preferably comprise of red onion juice present in an amount ranging from approximately 5 percent to approximately 30 percent of the total weight of the juice. Cucumber juice is present in an amount ranging from approximately 15 percent to approximately 80 percent of the total weight of the juice. Leafy green vegetable juice is present in an amount ranging from approximately 15 percent to approximately 80 percent of the total weight of the juice. Pineapple juice is present in an amount ranging from approximately 1 percent to approximately 40 percent of the total weight of the juice.

Preferably, the red onion juice is present at approximately 10 percent to approximately 25 percent of the total weight of the juice. Preferably, the cucumber juice is present at approximately 30 percent to approximately 70 percent of the total weight of the juice. Preferably, the leafy green vegetable juice is present at approximately 20 percent to approximately 60 percent of the total weight of the juice. Preferably, the pineapple juice is present at approximately 3 percent to approximately 25 percent of the total weight of the juice.

Most preferably, the red onion juice is present at approximately 14 percent of the total weight of the juice. Most preferably, the cucumber juice is present at approximately 47 percent of the total weight of the juice. Most preferably, the leafy green vegetable juice is present at approximately 30 percent of the total weight of the juice. Most preferably, the pineapple juice is present at approximately 9 percent of the total weight of the juice.

If the total weight of the juice contains less than 1 percent pineapple juice the drink will not have an improved flavor. If the total weight of the juice contains more than 40 percent pineapple juice the drink will be too acidic and may cause upset stomach and heartburn. If the total weight of the juice contains more than 40 percent pineapple juice, the pineapple juice will counteract the effects of the hangover treatment, the drink will lose potency, and the effectiveness of the drink will be reduced.

Figure 4:
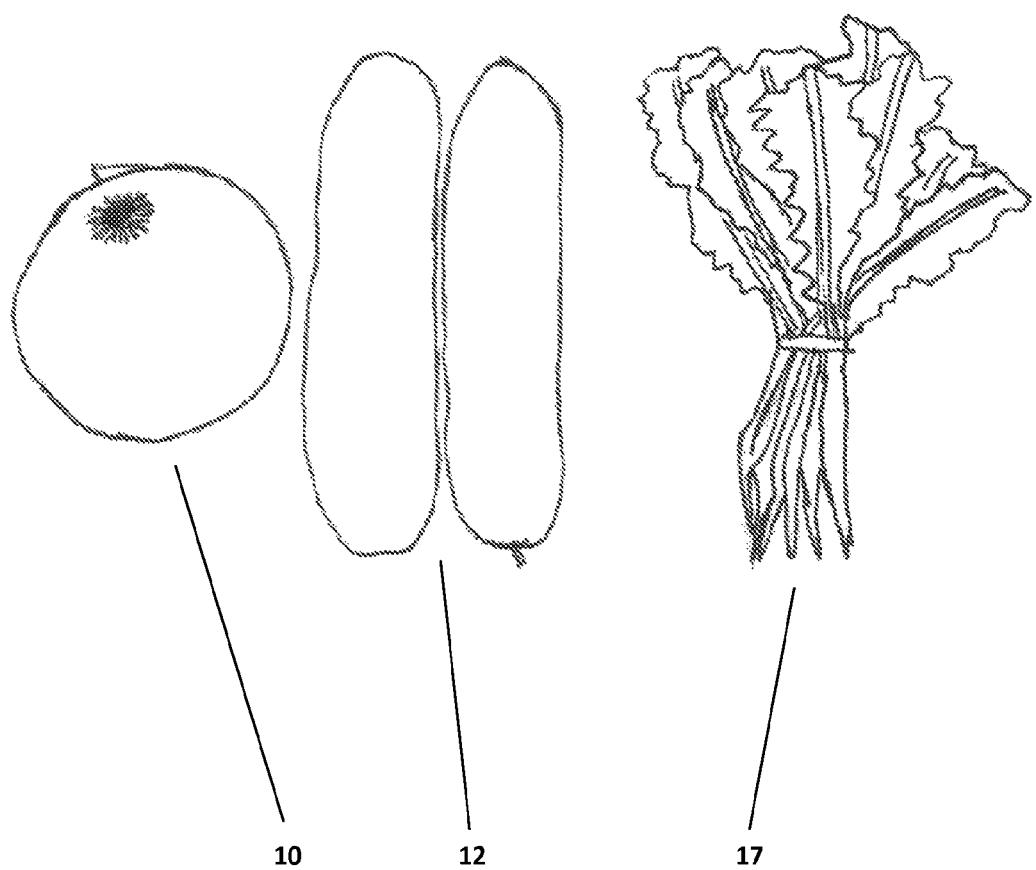
FIG. 4 shows raw elements for a fourth embodiment of the Hangover Treatment.

The process for making the juice 40 of the present invention is shown in FIG. 4. This process involves collecting red onions 10, cucumbers 12, and leafy green vegetables as raw materials 20. Romaine lettuce 14 may be washed 22. Red onion 10 may be chopped and cucumbers 12 may be peeled in preparation for juicing. Juicing is the process of extracting the liquid from a fruit or vegetable from the solid portion, by using a juicer. A juicer is a device or machine that separates the liquid portion of a fruit or vegetable from the solid portion (e.g. pulp), for example, with the use of a strainer, filter, or other device. Although some pulp may end up with the liquid portion, the intent is to create a juice. The cucumbers may be peeled to extract the light green flesh, which contains the medicinal properties. The roots of the onion may be chopped off because it does not contain juice and may contain dirt and bacteria. However, any ingredient may be added whole if the juicer has the capability and capacity.

In juicing 26, all prepared ingredients are juiced to create a juice composition containing approximately 10 to 25 percent red onion juice, approximately 20 to 60 percent leafy green vegetable juice, and approximately 30 to 70 percent cucumber juice, by weight. Preferably, freshly served 28, the juiced product can be sold fresh directly to the user for consumption. The juice may be pasteurized or undergo high pressure processing 30, so that the juice is treated to kill bacteria and can be bottled and stored for distribution. High pressure processing is preferable because it keeps more nutrients in the juice and can extend the shelf life longer than pasteurization can. In bottling 32, the product may be bottled and labeled. The product may be served fresh after juicing or may be processed and bottled for storage and distribution.

Red onion 10 causes the excretion of alcohol from the body which reduces alcohol levels in the blood. Red onion 10 also flushes out the digestive system which contains the byproducts of drinking, lessening the body's intake of harmful chemicals and reducing stress on the liver and kidneys. Because of this flush of the digestive system, red onion 10 promotes hunger as the digestive system regains normal functioning and processing. Red onion 10 also contains a powerful antioxidant which helps to thin the blood and lower cholesterol and can help reduce high blood pressure and help heart function. Red onion 10 helps heart function by boosting beneficial HDL cholesterol, thinning the blood, retarding blood clotting, lowering total blood cholesterol, lowering triglycerides, and lowering blood pressure. Red onion 10 also wards off blood clots and fights infections which can prevent and heal the damage caused by internal bleeding due to heavy drinking Red onion 10 is also anti-inflammatory, antibiotic, antiviral, and is thought to have diverse anti-cancer powers, all of which can help the body recover from the damaging effects of drinking alcohol. The antibiotic properties of red onion 10 help to destroy many disease-causing pathogens in the stomach including *E. coli* and *Salmonella* which may have been ingested during a night of drinking. The diverse anti-cancer powers of red onion 10 come from the antioxidants in the red onion 10 which can protect against cancer by reducing the DNA damage in cells caused by free radicals. This cancer prevention effect is helpful in preventing any further damage to the liver and may be helpful for the prevention of liver cancer. Red onion 10 also cleanses one's blood, body, and skin due to sulfur-containing amino acids found in onions that are able to detoxify one's body from heavy metals such as mercury, cadmium, and lead which are present in alcoholic beverages. This detoxification is important during a hangover because of the poisoning effect that heavy metals have on the body. Red onion 10 also contains a significant amount of sulfur, which is good for the liver. The liver is heavily affected by the consumption of alcohol and the sulfur found in red onion 10 can help promote normal liver function.

Cucumber 12 reduces the acidity of the stomach and coats the stomach and intestines to sooth. This reduces stomach pain, vomiting, and headaches while allowing for the digestive system to recover. After eating cucumber which is highly-alkaline, one's stomach and intestines regain a normal level of acidity, reducing stomach bleeding and pain. Cucumber 12 is an antacid and helps relieve heartburn, which is commonly experienced during an alcoholic hangover. Cucumber 12 is also known to dissolve kidney stones, which can develop due chronic alcohol consumption. Cucumber 12 is also known to stabilize the body's blood pressure. It has been found that patients of high or low blood pressure gain relief from eating cucumber 10. This blood pressure stabilization effect helps to reduce the abnormal blood pressure caused by drinking, which is experienced during an alcoholic hangover. Cucumber 10 also lowers uric acid levels in your system, which helps to keep one's kidneys healthy. Kidneys are negatively affected by drinking and cucumber 10 can help to reduce those negative effects experienced during a hangover. Cucumber 10 also reduces bad cholesterol. This reduction of bad cholesterol in the body promotes healthy heart function. Cucumber 10 is also a very good source of vitamin K, which can prevent cirrhosis of the liver by preventing vitamin K deficiency bleeding in the intestines and liver. Vitamin K deficiency can be caused by drinking alcohol in excess amounts and can lead to vitamin K deficiency bleeding in the intestines and liver while an individual is hung-over. Cucumber 10 is also a very good source of B vitamins, which can provide energy and reduce the fatigue felt during an alcoholic hangover. Cucumber 10 also helps to reduce headaches caused by hangovers because of the sugars, B vitamins, and electrolytes found in cucumber 10. The boost of energy received by cucumber 10 helps to reduce fatigue and muscular weakness experienced during an alcoholic hangover. Cucumber 10 also aids in healthy digestion as it is a remedy for individuals with chronic constipation. Because cucumber 10 helps with digestion it helps promote bowel movement. Bowel movement leads to defecation, which helps to cleanse the body of toxins by flushing them out of the digestive system. This flush of the digestive system helps to promote hunger and normal food consumption. Once the body's intestines have been emptied of non-nutrition bearing waste, there is available space in the body's intestines for healthy fresh foods to be ingested.

Romaine lettuce 14 is a very good source of vitamin K, which can prevent cirrhosis of the liver by preventing vitamin K deficiency bleeding in the intestines and liver. Vitamin K deficiency can be caused by drinking alcohol in excess amounts and can lead to vitamin K deficiency bleeding in the intestines and liver while an individual is hung-over. There is 100% or more RDA (recommended daily allowance) of vitamin K in an effective amount of the hangover drink. In a 10 ounce drink comprising of the most preferable percentage amounts of red onion juice, cucumber juice, and a leafy green vegetable juice there is approximately 250% RDA of Vitamin K. Romaine lettuce 14 is also a significant source of folate. Alcohol interferes with the absorption of folate, so persons who drink excessively are at risk for folate deficiency anemia. Signs of folate deficiency anemia include decreased appetite, irritability, lack of energy, and diarrhea. There is 30% or more RDA of folate in an effective amount of the hangover drink. In a 10 ounce drink comprising of the most preferable percentage amounts of red onion juice, cucumber juice, and a leafy green vegetable juice there is approximately 75% RDA of folate. Romaine lettuce 14 is also alkaline forming. Alcohol consumption causes the acid/alkaline balance of the body to become abnormal. The alkaline forming minerals in romaine lettuce 14 help remove toxins and keep one's acid/alkaline balance in order. Romaine lettuce 14 is also a very good source of vitamin A and beta-carotene. Alcohol consumption results in a significant depletion of hepatic vitamin A. There is 150% or more RDA of vitamin A in an effective amount of the hangover drink. In a 10 ounce drink comprising of the most preferable percentage amounts of red onion juice, cucumber juice, and a leafy green vegetable juice there is approximately 375% RDA of Vitamin A. Depletion of hepatic vitamin A can lead to fatty liver, alcoholic hepatitis, and cirrhosis of the liver. Beta-carotene is a precursor to vitamin A and allows for vitamin A absorption. Since romaine lettuce 14 contains high levels of vitamin A and beta-carotene, consumption of romaine lettuce 14 is effective for treating this deficiency. Beta-carotene in food is safe for alcohol drinkers, but it is toxic for alcohol drinkers when it is taken as a pill supplement. In alcohol drinkers, there is a toxic reaction that occurs between beta-carotene supplements and ethanol. Thus, food and juice consumption is the only way to safely recover from a vitamin A deficiency. Early symptoms of liver disease include fatigue and loss of energy, poor appetite and weight loss, and nausea or belly pain. These symptoms are effectively treated with romaine lettuce 14.

Romaine lettuce 14, however, can be substituted for one or more raw leafy greens including butterhead lettuce 15, oakleaf lettuce 16, turnip greens 17, or spinach 18. All of these leafy greens contain similar levels of vitamin A, beta-carotene, vitamin K, and folate.

Figure 5:
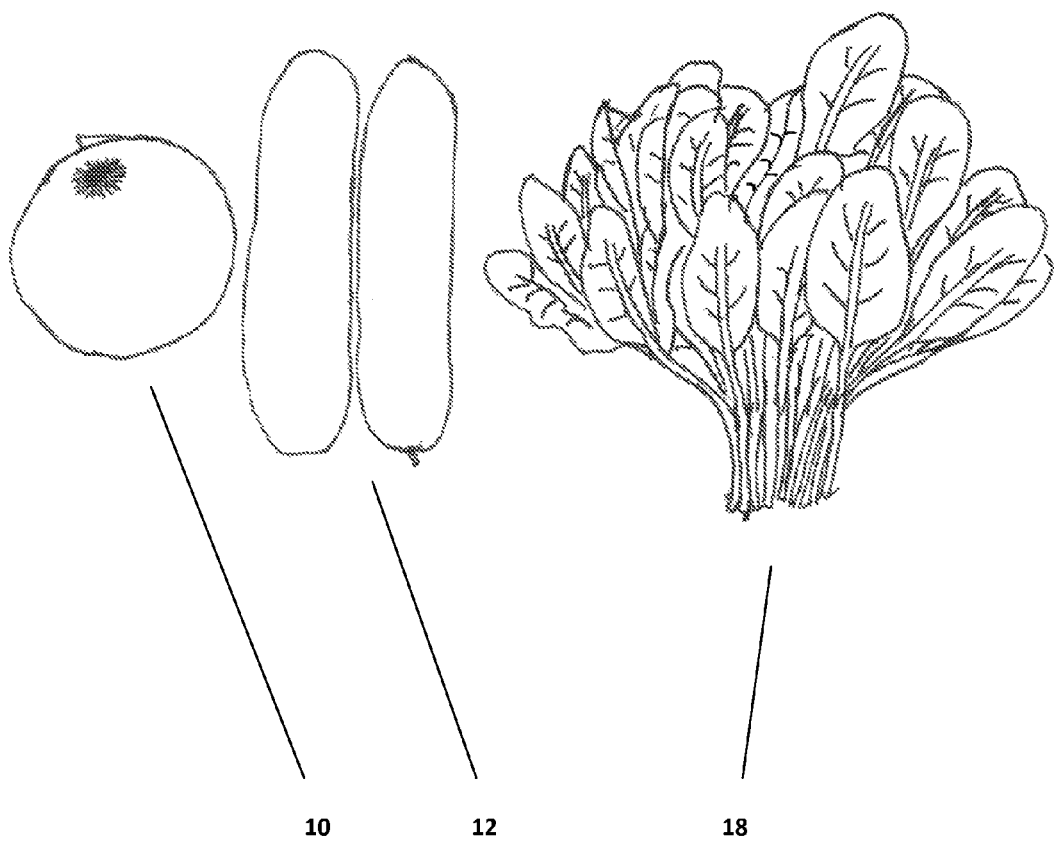
FIG. 5 shows raw elements for a fifth embodiment of the Hangover Treatment.
Figure 6:
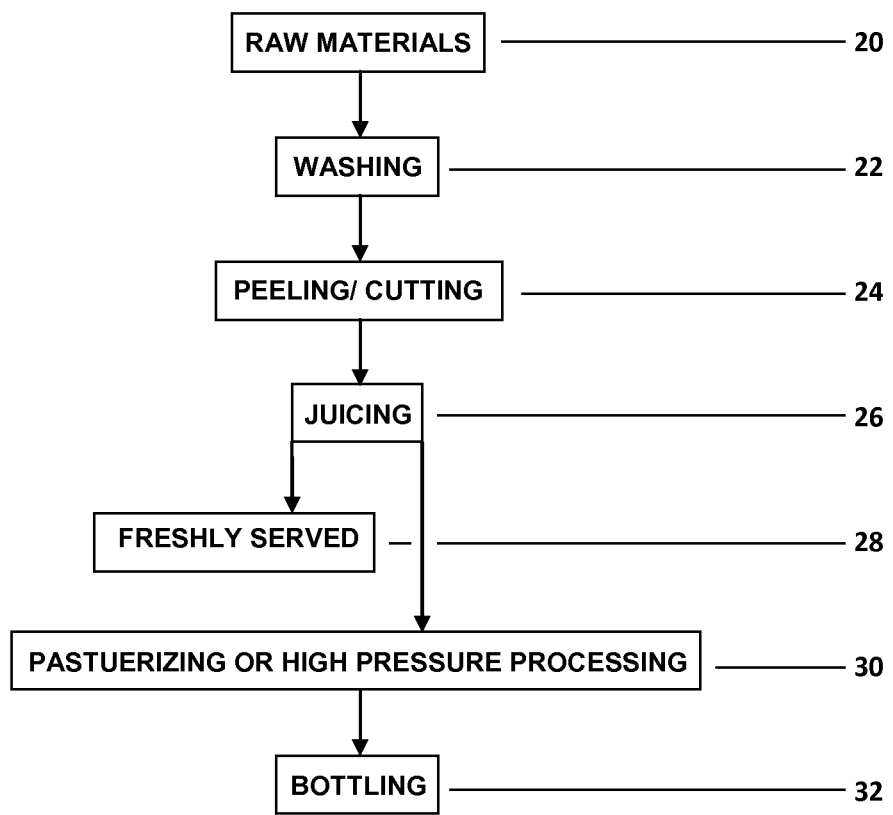
FIG. 6 shows a flow diagram of an embodiment of the procedure for preparing the Hangover Treatment.
Figure 7:
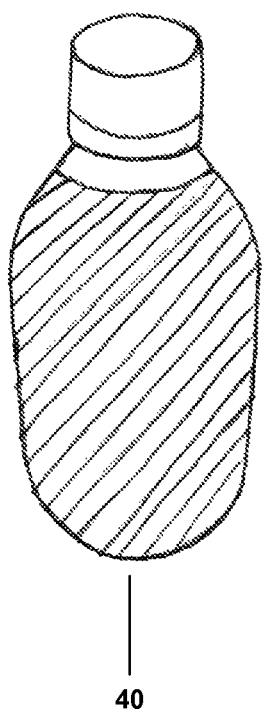
FIG. 7 is an embodiment of the final juice product.

Juice drink 40 in FIG. 5 is one embodiment of the final hangover treatment sold to consumers. The manner of using the product will be the same for all embodiments. Preferably, the hangover treatment is used in the morning after drinking when the hangover symptoms are present. Preferably, the product should first be completely consumed within a short period of time (within about five minutes). After drinking the product, it is preferable that one does not lie down horizontally for approximately 30 minutes in order to allow the juice to run through one's system. It will coat one's stomach and stomach pain will immediately begin to subside. During this approximate 30-minute period, one should not drink or consume anything except for water. If the mixture is thrown up, a second dose will have to be consumed. If one feels like throwing up or is sick to the stomach for more than thirty minutes after taking the hangover drink, it may be best to throw up and take another dose. There may be a backup of bile from the liver inside one's stomach (due to excessive drinking) and this bile needs to be cleaned out before one can properly digest the hangover drink. This is a common problem called bile reflux where there is a backflow of bile into the stomach from the bile tract that connects to the liver and gallbladder.

The hangover treatment will alleviate hangover symptoms by cleansing out the body and filtering out the toxins, while replacing nutrients. If the amount of nutrients lost is significant, then the effective amount of the composition an individual will need to consume will be more than if the individual had lost fewer nutrients from drinking alcohol.

If the individual has been drinking for multiple days, this will also affect the amount of nutrients lost from the body and will increase the effective amount of the hangover treatment that is necessary to treat the individual's hangover symptoms. Hangover symptoms will be more severe and a larger dose of the hangover treatment will need to be consumed.

Alcohol is a diuretic, meaning that it increases urination. This increased urination decreases the normal levels of potassium in the body as potassium is lost during urination. To regain normal levels, it is advised to consume non-acidic foods high in potassium throughout the day such as cantaloupe, banana, watermelon, honey dew melon, potatoes, beans, milk, yogurt, cottage cheese, chicken, turkey, salmon, cod, flounder, beef, wheat bread, whole grains, brown rice, and bran. The foods mentioned above should be consumed intermittently throughout the day even after symptoms have subsided. The body increases levels of potassium in the body very slowly and it may take up to 24 hours for the body to obtain sufficient and stable potassium levels.

One should avoid eating any foods or food products containing high-acid fruits or vegetables such as tomatoes, grapefruits, limes, lemons, kiwis, olives, or pickles. These acidic fruits and vegetables will upset the stomach and reverse the beneficial effect of the hangover treatment. One should also not eat greasy foods, such as anything fried or deep fried, within 24 hours of using the hangover treatment. The oil in greasy foods sticks to the stomach lining and makes it more difficult for the body to absorb nutrients, which the body needs during a hangover. Greasy foods would also increase the body's blood pressure, which would counter the health effects of the hangover treatment. One should also avoid eating any tomato-based foods at any time while using the hangover treatment and up to 24 hours after consumption. Tomatoes are very difficult for the body to process and are very acidic. Tomato-based products will add stress to the body, increase the symptoms of the hangover, and counter the effects of the hangover treatment.

The standard time it takes to alleviate the symptoms of a hangover is about four hours from time of consumption. If a hangover persists, one should use another dose of the hangover treatment. The hangover treatment acts like a cleanse for one's body and so the process is a gradual improvement over time. It is not like headache medicine which reduces symptoms for a certain period of time. The hangover treatment effectively eradicates the hangover. Since the hangover treatment brings on a gradual improvement to one's body, it is recommended to go outdoors for fresh air and sun light. Fresh air and sunlight help to sooth one's body while the hangover treatment takes effect.

An advantage of Applicant's hangover drink is that the effective amount of the ingredients is normally too much to be eaten when not in juice form. The actual mass of the ingredients that must be consumed is more than most individuals can consume in a single sitting because it is too much food to be consumed into one's stomach. When an individual drinks the juice it is a reduction of mass of the raw ingredients without a reduction of the amount of nutrients obtained from the raw ingredients. The fibers and non-juice able matter is removed and the juice product is thus significantly reduced in volume as compared to the volume of the raw ingredients.

The juice composition of the hangover treatment allows one's body to process the nutrients more quickly and effectively than in its raw form because the nutrients can be obtained without breaking down the fibers and pulp of the ingredients. This means that the hangover symptoms will be treated more quickly and effectively.

The juice composition is also much more easily consumed because it involves no chewing. When an individual is hungover, the individual is fatigued and will have a hard time chewing. In order to consume an effective amount of the hangover treatment in its raw form the individual may have to chew for 20 minutes and up to an hour. This is very difficult for an individual that is hungover. The juice composition can be consumed within less than a minute if gulped down and within seconds if a straw is used to drink the composition.

The juice composition is also less potent in smell and will leave behind less of a smell in an individual's mouth than if the ingredients are consumed in raw form because of the amount of time of contact to the gum and teeth area. When the juice is consumed, it is swallowed quickly and leaves behind minimal onion smell. If an individual were to eat the raw ingredients, he or she would have to thoroughly chew the ingredients for up to an hour and this smell would linger in the mouth even after flossing, brushing with toothpaste, and rinsing with mouthwash.

The juice composition is more easily consumed than a blended product of the raw ingredients because the pulp of the ingredients is very thick and cannot be consumed by an individual without extreme difficulty. The consistency of the raw ingredients when blended is that of a thick clumpy salsa. The composition of raw ingredients when blended is very harsh in flavor and the effective amount necessary to alleviate a hangover is too massive for an individual to consume in one sitting.

Applicant's invention comprises ingredients that are widely produced and readily available year round in the United States. The hangover drink can be produced at any time during the year because red onion, cucumber, and leafy green vegetables are not seasonal and are harvested and sold year round.

Applicant's invention is useable in any environment without preparation making it portable and widely saleable. It comprises ingredients that are not seasonal and are sold year round. It can be produced in many regions of the world because of the wide availability of red onion, cucumber, and other leafy greens. All ingredients are already recognized to be safe for consumption making the hangover treatment approvable by the FDA. It helps to reduce the effects of withdrawals from alcohol poisoning making it a likely treatment of alcoholism. It is easier to consume as a drink then in its raw elements. It more effectively coats the stomach as a drink than it does when consumed in its raw elements, reducing the acidity and soothing the stomach more quickly. It is consumed as a liquid drink, which minimizes both the strength of the products odor in the mouth and length of time the products odor is present in the mouth. If the raw ingredients are consumed by chewing, an unpleasant odor lingers in the mouth that is hard to remove and can last for many hours. It can be consumed without cutting red onion, which can irritate the eyes. It is rapidly processed by the body in juice form as the body does not have to break down the pulp of the product to process the nutrients.

Figure 2:
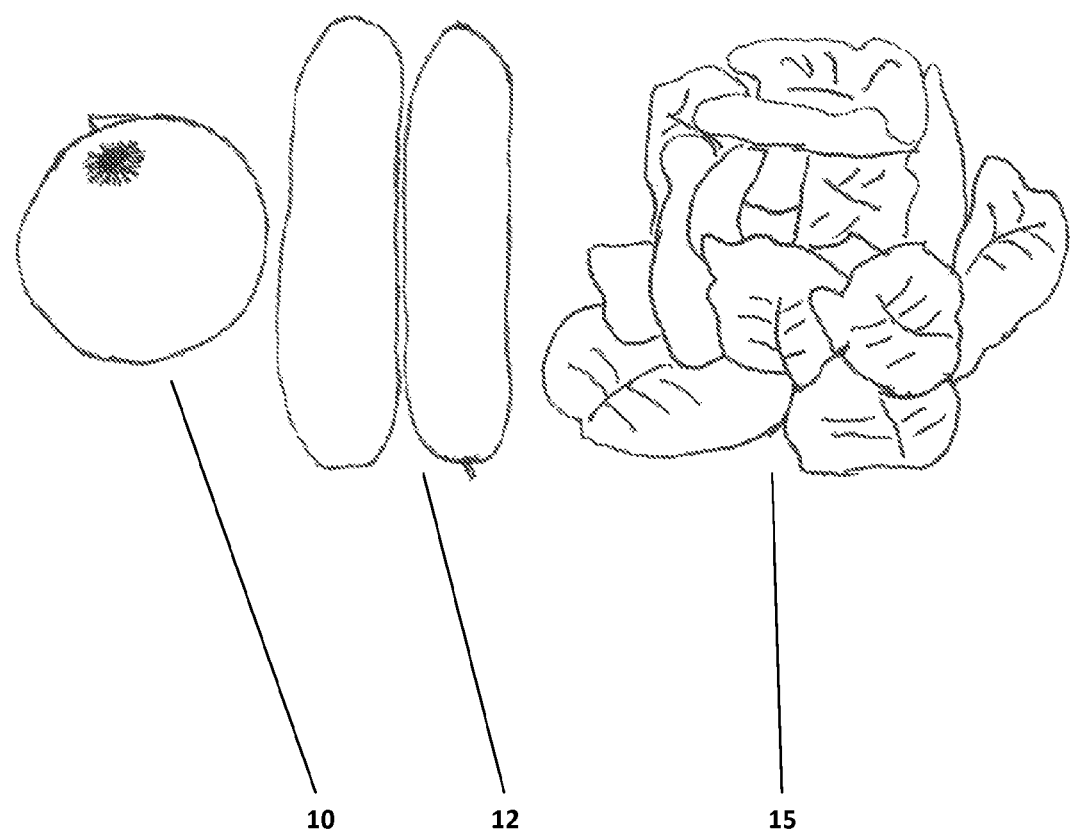
FIG. 2 shows raw elements for a second embodiment of the Hangover Treatment.
Figure 3:
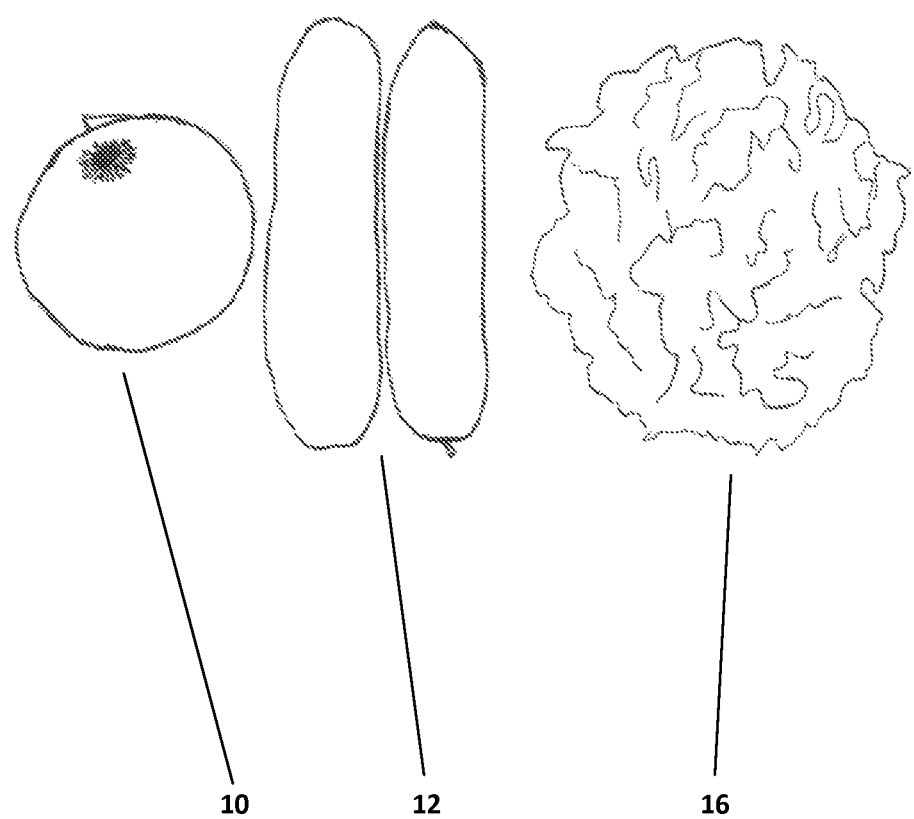
FIG. 3 shows raw elements for a third embodiment of the Hangover Treatment.

There are various possibilities with regard to the relative disposition of the third element of the hangover treatment. To create other embodiments of the hangover treatment, romaine lettuce 14 as shown in FIG. 1 can be substituted for one or more raw leafy greens, including butterhead lettuce 15, oakleaf lettuce 16, turnip greens 17, or spinach 18. All of these leafy greens contain similar high amounts of vitamin A, beta-carotene, vitamin K, and folate. FIG. 2 is another embodiment containing butterhead lettuce 15 as the third leafy green. FIG. 3 is another embodiment containing oakleaf lettuce 16 as the third leafy green. FIG. 4 is another embodiment containing turnip greens 17 as the third leafy green. FIG. 5 is another embodiment containing spinach 18 as the third leafy green.

Although the third vegetable may be different for each embodiment, the first two elements, red onion 10 and cucumber 12, remain the same. Future embodiments may also include flavorings, which may or may not have any health benefits. Flavorings for new embodiments may be added and may change with market preferences and after ongoing market research. Flavorings for future embodiments may include pineapple juice.

EXAMPLE #1

Dates of Experiment

8/15/2013, 8/18/2013, 8/20/2013, 8/31/2013, 9/3/2013, 9/7/2013, 9/8/2013, 9/12/2013

Purpose

This study was performed to test "the Composition and Method for Treating a Hangover" in order to test its effectiveness. This study was performed on ten participants of various age and sex. The study was done the following day after consumption of alcohol. The participants were no longer intoxicated at the time of the study and were experiencing hangovers of different severity and intensity. Each participant consumed one 10 ounce drink comprising, by weight of the juice, 10-25% red onion juice, 20-60% romaine lettuce juice, and 30-70% cucumber juice. It was my hypothesis that the hangover symptoms would be majorly reduced or completely eliminated within a span of four hours from the time of consumption of the composition.

Materials

A single 10 ounce drink per participant which contains the first embodiment of the composition (Red Onion Juice, Cucumber Juice, and Romaine Lettuce Juice)
A Hangover study questionnaire Procedure 1) Direct each participant to fill out the first page of the study and answer questions 1-6 of the study.
    Question #1: How many days a week do you drink 4 or more alcoholic beverages?
    Question #2: On the nights you drink 4 or more alcoholic beverages, How many drinks do you normally consume in an average night?
    Question #3: What types of alcoholic drinks do you normally consume in a night (beer, liquor, wine)?
    Question #4: On nights when you drink 4 or more alcoholic beverages, how many of those nights typically result in a hangover the next day?
    Question #5: How did you feel before taking the Hangover Drink? What are your ailments (i.e. weak stomach, vomiting, upset stomach, acidic stomach, nausea, dehydration, elevated body temperature, high blood pressure, rapid heart rate, heart palpitations, difficulty concentrating, bloodshot eyes, trouble sleeping, depression, anxiety, irritability, sensitivity to light and noise, blurred vision, dizziness, cold sweats, muscular weakness, fatigue, muscle aches, general pain, labored breathing, erratic motor functions, headache etc..)?
    Question #6: On a scale of 1 to 10, with 1 being the least hung-over and 10 being the most hung-over, how hung-over would you say you felt before taking the hangover drink?
2) Give each participant the ten ounce drink and direct them to drink it. Make sure it is completely consumed within 5 minutes.
3) Five minutes after consumption, direct each participant to fill out question 7.
    Question #7: How did you feel within the first 5 minutes of taking the Hangover Drink?
4) One hour after consumption, direct each participant fill out question 8.
    Question #8: How did you feel one hour after taking the Hangover Drink? Have any of your ailments been reduced? By how much?
5) Two hours after consumption, direct each participant to fill out question 9.
    Question #9: How did you feel 2 hours after taking the Hangover Drink? Have any of your ailments been reduced? By how much?
6) Four hours after consumption, direct each participant to fill out questions 10-12 and sign the questionnaire.
    Question #10: How did you feel 4 hours after taking the Hangover Drink?
    Question #11: Do you believe that the Hangover Drink had an effect on the severity and length of your hangover? If so, please explain how you felt and what difference the hangover drink made.
    Question #12: If you had the opportunity to use this product in the future, how likely would you decide to use it on a scale of 1 to 10 with one being least likely to use it and 10 being the most likely to use it?
7) If any additional results were noticed after the allotted 4 hours of the study, the participant should add those comments along with the number of hours these results were noticed after consumption.

Results

In example #1, 10 participants had been drinking alcohol in the prior night and were no longer intoxicated, but were experiencing hangovers of different severities on scale of 1 to 10, with 1 being the least hungover and 10 being the most. Results of the study are shown in FIG. 8. The average number of drinks consumed in the prior night by the participants was 9 drinks and the average age of the participants was 29 years of age. The average hangover was at a severity of level 6 before taking Applicant's hangover drink. The next morning, the subjects were given 10 ounces of Applicant's hangover drink.

After the participants were given the 10-ounce serving of the Applicant's hangover drink and were examined to determine what hangover symptoms were alleviated by the Applicant's hangover drink, how long it took for the hangover drink to have a beneficial effect, and how long until the Applicant's hangover drink alleviated the hangover completely. Fifty percent of participants felt an improvement in their symptoms within the first 5 minutes after consumption. Eighty percent of participants felt an improvement within the first hour after consumption and 100% of participants felt an improvement in their symptoms within the first 2 hours after consumption. While, the average time a hangover will last for most individuals can range from 8 hours to 48 hours, 10% of participants were relieved of their hangover around 1 hour after consumption, 70% of participants were relieved of their hangover around 4 hours after consumption, and 10% of participants were relieved of their hangover around 6 hours after consumption. The 1 other participant (10% of the participants) who did not have complete hangover relief had a hangover reduction from a maximum level 10 out of 10 to a hangover of level 3 out of 10. One hundred percent of participants stated that the drink made a difference in the severity and length of their hangover.

One participant said that she remained hung-over only because she "did not have any more" of the hangover drink to consume. If this participant had been given a larger serving of the hangover drink to begin with or was given a second subsequent serving, her hangover may have subsided like the rest of the participants within the 4 hour standard period. This study proves that the applicant's invention is effective for the purpose of relieving hangover symptoms.

EXAMPLE #2

Dates of Experiment

5/24/2014, 5/25/14, 5/26/14, 5/27/14, 5/31/14, 6/1/14, 6/2/14, 6/7/14, 6/8/14, 6/9/14, 6/14/14, 6/15/14, 6/16/14, 6/21/14, 6/22/14, 6/23/14, 7/5/14, 7/12/14, 7/13/14, 7/14/14, 8/2/14, 8/3/14, 8/4/14, 8/9/14, 8/10/14, 8/11/14, 8/16/14, 8/17/14, 8/18/14, 8/23/14, 8/24/14, 8/25/14, 8/30/14, 9/1/14, 9/2/14, 9/06/14, 9/7/14, 9/8/14, 9/13/14, 9/14/14, 9/15/14, 9/20/14, 9/21/14, 9/22/14, 9/27/14, 9/28/14, 9/29/14, 10/04/14, 10/05/14, 10/11/14, 10/12/2014

Purpose

This study will be performed to test "the Composition and Method for Treating a Hangover" in order to test and compare the effectiveness of a drink comprising of the first embodiment of the hangover drink with a drink consisting essentially of, by weight of the composition, 100% romaine lettuce juice, a drink consisting essentially of, by weight of the composition, 100% cucumber juice, a drink consisting essentially of, by weight of the composition, 100% red onion juice, and a drink comprising a combination of the first embodiment of the hangover drink and flavoring comprising of, by weight of the composition, 3 percent to 25 percent juiced pineapple. This study will be performed on participants of various age and sex. The study will be done the following day after consumption of alcohol. The participants will no longer be intoxicated at the time of the study and will be experiencing hangovers of different severity and intensity. Each participant will consume one 10 ounce drink. Each drink will be labeled with a number between 1 and 5. The participants will not know which drink of the five they are consuming and will be asked to be as objective as possible when making their analysis of the drink during the questions portion of the study. Those participants that will be given drink labeled number 1 to consume, will consume a drink consisting essentially of, by weight of the juice, 100% romaine lettuce juice. Those participants that will be given drink labeled number 2 to consume, will consume a drink consisting essentially of, by weight of the juice, 100% cucumber juice. Those participants that will be given drink labeled number 3 to consume, will consume a drink consisting essentially of, by weight of the juice, 100% red onion juice. Those participants that will be given drink labeled number 4 to consume, will consume a drink comprising, by weight of the juice, 10-25% red onion juice, 20-60% romaine lettuce juice, and 30-70% cucumber juice. Those participants will be given drink labeled number 5 to consume, will consume a drink comprising, by weight of the juice, 10-25% red onion juice, 20-60% romaine lettuce juice, 30-70% cucumber juice, and 3-25% pineapple juice. It is my hypothesis, that for those participants that consume drink number 4 and 5, their hangover symptoms will be majorly reduced or completely eliminated within a span of four hours from the time of consumption of the composition. It is also my hypothesis that those who consume drink number 1, 2, and 3 will see some improvement, but will not have a major reduction or complete reduction of their hangover symptoms and that their hangovers will continue after the 4 hour period allotted for the hangover drink study.

Materials to be Used

A single 10 ounce drink per participant which contains by weight of the juice, either 100% romaine lettuce juice, or 100% cucumber juice, or 100% red onion juice, or the first embodiment of the hangover treatment (10-25% red onion juice, 20-60% romaine lettuce juice, and 30-70% cucumber juice), or the first embodiment of the hangover treatment with additional flavoring of pineapple juice (10-25% red onion juice, 20-60% romaine lettuce juice, 30-70% cucumber juice, and 3-25% pineapple juice).

A hangover study questionnaire

Procedure to be Followed

1. Direct each participant to fill out the first page of the study and answer questions 1-6 of the study.
    Question #1: How many days a week do you drink 4 or more alcoholic beverages?
    Question #2: On the nights you drink 4 or more alcoholic beverages, how many drinks do you normally consume in an average night?
    Question #3: What types of alcoholic drinks do you normally consume in a night (beer, liquor, wine)?
    Question #4: On nights when you drink 4 or more alcoholic beverages, how many of those nights typically result in a hangover the next day?
    Question #5: How did you feel before taking the Hangover Drink? What are your ailments (i.e. weak stomach, vomiting, upset stomach, acidic stomach, nausea, dehydration, elevated body temperature, high blood pressure, rapid heart rate, heart palpitations, difficulty concentrating, bloodshot eyes, trouble sleeping, depression, anxiety, irritability, sensitivity to light and noise, blurred vision, dizziness, cold sweats, muscular weakness, fatigue, muscle aches, general pain, labored breathing, erratic motor functions, headache, inability to eat solid foods, lack of hunger etc..)?
    Question #6: On a scale of 1 to 10, with 1 being the least hung-over and 10 being the most hung-over, how hung-over would you say you felt before taking the hangover drink?
2. Give each participant the ten ounce drink and direct them to drink it. Make sure it is completely consumed within 5 minutes.
3. Five minutes after consumption, direct each participant to fill out question 7.

Question #7: How did you feel within the first 5 minutes of taking the Hangover Drink? Do you feel a reduction in your hangover? If so how would you rate your hangover on a scale from 1-10?

4. One hour after consumption, direct each participant fill out question 8.

Question #8: How did you feel one hour after taking the Hangover Drink? Have any of your ailments been reduced? How would you rate your hangover on a scale from 1-10?

5. Two hours after consumption, direct each participant to fill out question 9.

Question #9: How did you feel 2 hours after taking the Hangover Drink? Have any of your ailments been reduced? How would you rate your hangover on a scale from 1-10?

6. Four hours after consumption, direct each participant to fill out questions 10-12 and sign the questionnaire.

Question #10: How did you feel 4 hours after taking the Hangover Drink? Have any of your ailments been reduced? How would you rate your hangover on a scale from 1-10?

Question #11: Did the hangover drink have a positive effect on your general health and well being? Did the hangover drink make a significant impact on your hangover and all its symptoms as a whole? If so, please explain how you felt and what difference the hangover drink made.

Question #12: If you had the opportunity to use this product in the future, how likely would you decide to use it on a scale of 1 to 10 with one being least likely to use it and 10 being the most likely to use it?

7. If any additional results were noticed after the allotted 4 hours of the study, the participant should add those comments in question #13 along with the number of hours these results were noticed after consumption of the drink.

Speculative Results

I think that the participants of the study that will consume a drink consisting essentially of, by weight of the juice, 100% juiced cucumber, will feel a reduction in the acidity and discomfort in their stomach. They will also have bowel movement and be able to defecate. They will regain their ability to eat solid foods and their headaches may be reduced. Although I believe their symptoms will decrease in severity, I think their hangovers will not be relieved or completely reduced after four hours from the time of consumption of the juiced cucumber drink. I think that the participants will feel that the drink helped to reduce their symptoms, but that it did not make a significant impact on their hangover and all its symptoms as a whole. I think that the drink will have a positive effect on their general health and well being, but that it will not cure their hangover symptoms completely.

I think that the participants of the study that will consumed a drink consisting essentially of, by weight of the juice, 100% juiced romaine lettuce, will feel that their fatigue and lack of energy will be reduced. They will be able to regain an appetite for food and there will be a reduction in their nausea and belly pain. Although I think their symptoms will be reduced, their hangovers will not be relieved or completely reduced after four hours from the time of consumption of the juiced romaine lettuce drink. I think the participants will feel that the drink had helped to reduce their symptoms, but that it did not make a significant impact on their hangover and all its symptoms as a whole. The drink will have a positive effect on their general health and well being, but it will not cure their hangover symptoms completely.

I think the participants of the study that will consume a drink consisting essentially of, by weight of the juice, 100% juiced red onion juice, will feel less dizzy, better able to focus, and better able to concentrate. They will be able to sleep or relax because their body will become more relaxed, their heart rate will be reduced to a normal rate from a rapid heart rate, and they will become less irritable. Their eyes will become less bloodshot and red, and their vision will become clearer. I think their digestive system will be flushed out and will lead to consumption and hunger for solid foods. Some participants will not be able to drink the juiced red onion drink without throwing up. The participants that will throw up, will feel better after throwing up, but will not be cured of their hangover symptoms. Symptoms will be reduced for those who do not throw up the drink, but their hangovers will not be relieved or completely reduced after four hours from the time of consumption of the juiced red onion drink. The participants will feel that the drink helped to reduce their symptoms, but that it did not make a significant impact on their hangover and all its symptoms as a whole. I think the drink will have a positive effect on their general health and well being, but that it will not cure their hangover symptoms completely.

I think that the participants of the study that will consume a drink comprising, by weight of the juice, 10-25% juiced red onion, 20-60% juiced romaine lettuce, and 30-70% juiced cucumber, will feel a major reduction in most or all of their hangover symptoms or will be completely cured of their hangover within a span of 4 hours from the time of consumption of the juiced drink.

I think that the participants of the study that will consume a drink comprising, by weight of the juice, 10-25% juiced red onion, 20-60% juiced romaine lettuce, 30-70% juiced cucumber, and 3-25% juiced pineapple will feel a major reduction in most or all of their hangover symptoms or will be completely cured of their hangover within a span of 4 hours from the time of consumption of the juiced drink.

This study will prove that both the applicant's invention and the applicant's invention including flavoring are effective for the purpose of relieving hangover symptoms. This study will also prove that the components of the applicant's invention create a novel synergistic effect because the combination creates a greater effect than the sum of the effects of the components separately.

While the above description contains much specificity, it should not be construed as limitations on the scope, but rather as an exemplification of several embodiments thereof Many other variations are possible. Accordingly, the scope should be determined not by the embodiments illustrated, but by the appended claims and their legal equivalents.

What is claimed is:

1. A method for treating a hangover, comprising administering to a subject in need thereof a composition comprising:
   a. juiced red onions present in an amount of approximately 5 percent to approximately 30 percent of a total weight of the composition;
   b. juiced cucumbers present in an amount of approximately 15 percent to approximately 80 percent of the total weight of the composition; and
   c. juiced romaine lettuce present in an amount of approximately 15 percent to approximately 80 percent of the total weight of the composition; and
   whereby the hangover is alleviated.

2. The method of claim 1, wherein the composition is administered every 4 hours as needed.

3. The method of claim 1, wherein the composition is administered when the subject is no longer intoxicated, but while the subject still has the hangover.

4. The method of claim 1, wherein the composition is administered on a morning after a night of drinking alcohol.

5. The method of claim 1, wherein the composition is administered after the subject has fallen asleep and has woken up.

6. A method for treating a hangover in a subject in need thereof, comprising consuming approximately 2 ounces to approximately 20 ounces of a composition comprising:
   a. juiced red onions present in an amount of approximately 5 percent to approximately 30 percent of a total weight of the composition;
   b. juiced cucumbers present in an amount of approximately 15 percent to approximately 80 percent of the total weight of the composition; and
   c. juiced romaine lettuce present in an amount of approximately 15 percent to approximately 80 percent of the total weight of the composition;
   whereby the hangover is alleviated.

7. The method of claim 6, wherein the composition is administered every 4 hours as needed.

8. The method of claim 6, wherein the composition is administered when the subject is no longer intoxicated, but while the subject still has the hangover.

9. The method of claim 6, wherein the composition is administered on a morning after a night of drinking alcohol.

10. The method of claim 6, wherein the composition is administered after the subject has fallen asleep and has woken up.

11. A method for treating a hangover, comprising administering to a subject in need thereof a composition comprising:
   a. juiced red onions present in an amount of approximately 5 percent to approximately 30 percent of a total weight of the composition;
   b. juiced cucumbers present in an amount of approximately 30 percent to approximately 70 percent of the total weight of the composition;
   c. juiced romaine lettuce present in an amount of approximately 20 percent to approximately 60 percent of the total weight of the composition; and
   d. pineapple juice present in an amount of approximately 1 percent to approximately 40 percent of the total weight of the composition, whereby the hangover is alleviated.

12. The method of claim 11, wherein the pineapple juice is present at approximately 3 percent to about 25 percent of the total weight of the composition.

13. The method of claim 11, wherein the juiced red onions is present in an amount of approximately 10 percent to approximately 25 percent of the total weight of the composition.

14. The method of claim 11, wherein the pineapple juice is present at approximately 3 percent to about 25 percent of the total weight of the composition, and wherein the juiced red onions is present in an amount of approximately 10 percent to approximately 25 percent of the total weight of the composition.

15. The method of claim 11, wherein the composition is administered every 4 hours as needed.

16. The method of claim 11, wherein the composition is administered when the subject is no longer intoxicated, but while the subject still has the hangover.

17. The method of claim 11, wherein the composition is administered on a morning after a night of drinking alcohol.

18. The method of claim 11, wherein the composition is administered after the subject has fallen asleep and has woken up.

* * * * *